United States Patent [19]

Habermeier et al.

[11] 4,171,424

[45] Oct. 16, 1979

[54] POLYESTERS CONTAINING UNITS DERIVED FROM METAL SALTS OF N-HYDROXYALKYLATED BRANCHED α-AMINOACIDS

[75] Inventors: Jürgen Habermeier, Pfeffingen, Switzerland; Godwin Berner, Fürth, Fed. Rep. of Germany

[73] Assignee: Ciba-Geigy Corporation, Ardsley, N.Y.

[21] Appl. No.: 887,272

[22] Filed: Mar. 16, 1978

Related U.S. Application Data

[62] Division of Ser. No. 673,238, Apr. 2, 1976, Pat. No. 4,093,639.

[30] Foreign Application Priority Data

Apr. 14, 1975 [CH] Switzerland .................... 4719/75

[51] Int. Cl.$^2$ ............................................. C08G 63/68
[52] U.S. Cl. ............................. 528/292; 260/45.75 C; 260/45.75 N; 260/45.75 M; 260/45.75 W; 528/273; 528/280; 528/281; 528/288; 528/289; 525/437; 525/447

[58] Field of Search ............... 528/273, 280, 281, 288, 528/289, 292; 260/45.75 C, 45.75 N, 45.75 M, 45.75 W

[56] References Cited

U.S. PATENT DOCUMENTS

| | | | |
|---|---|---|---|
| 3,153,011 | 10/1964 | Scruggs | 528/281 |
| 3,297,650 | 1/1967 | Halmi et al. | 528/277 |
| 3,385,830 | 5/1968 | VomOrde et al. | 528/275 |
| 3,563,956 | 2/1971 | Hilaire | 528/281 |

*Primary Examiner*—Lucille M. Phynes
*Attorney, Agent, or Firm*—Luther A. R. Hall

[57] ABSTRACT

Metal complexes of zinc, copper, cobalt and nickel and N-β-hydroxyalkylated or γ-aminoalkylated α-aminocarboxylic acids which are substituted at the α-carbon atom have excellent heat resistance, in particular a good heat resistance under oxydative influences. These complexes are also soluble in many starting components used for obtaining specific polymers. They are therefore especially suitable for obtaining copolymers which contain metal ions, for example polyesters, polyurethanes and polyamides. The copolymers can be used for manufacturing moulded articles.

14 Claims, No Drawings

POLYESTERS CONTAINING UNITS DERIVED FROM METAL SALTS OF N-HYDROXYALKYLATED BRANCHED α-AMINOACIDS

This is a divisional of application Ser. No. 673,238, filed on Apr. 2, 1976, now U.S. Pat. No. 4,093,639, issued on June 6, 1978.

The present invention provides metal complexes obtained from N-hydroxyalkylated or aminoalkylated, branched α-aminocarboxylic acids and divalent metal cations.

Metal complexes are known in the art as dyes and pigments. They have also attained importance in the form of chelate polymers. A prerequisite for the use of metal complexes as intermediates for obtaining polymers or as additives is their resistance to heat under the manufacturing or processing conditions, especially under oxydative influences.

Metal complexes of 2-hydroxyethyl-α-aminoacetic acid and suitable divalent metal ions of which, for example, iron, copper, nickel and zinc complexes are known, possess two free hydroxyl groups. On account of this diol function these metal complexes are of particular interest for the manufacture of linear and also thermoplastic polyesters.

For example, the polycondensation of nickelbis-(β-hydroxyethylglycine) with phthalic anhydride in vacuo at 170° C. is described in "Gummi, Asbest, Kunststoffe", 1962, page 974. However, in this process only insoluble and infusible oligomers are obtained, and no higher molecular weights are obtained. A further disadvantage is that, in the anhydride method, the choice of starting products is in general restricted to dicarboxylic acids which are able to form inner anhydrides, since when using mixed anhydrides break-off-reactions can prematurely prevent the chain formation. A stable metal complex with diol functions which is suitable for obtaining polyesters by means of straightforward, economic processes, such as the polycondensation of dicarboxylic acid diesters and diols in the melt and/or solid phase at temperatures of above app. 200° C., or by the acid chloride method, has not been described hitherto.

The present invention has for its object the provision of soluble metal complexes of α-aminocarboxylic acids with diol function or diamine function which have a sufficiently high resistance to heat, especially under oxydative influences, and which are suitable primarily for obtaining chelate polymers by the conventional economic processes and can be used in particular as co-components.

It is a further object of the invention to provide soluble and fusible polymers which can be processed by the customary methods of processing, for example injection moulding or extrusion, to give moulded articles of all kinds.

Accordingly, the invention provides metal complexes of N-hydroxyalkylated or aminoalkylated, branched α-aminocarboxylic acids and divalent metal cations, of the formula I

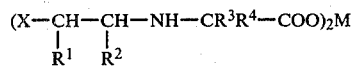  (I)

wherein
X represents hydroxyl or aminomethyl, $R^1$ represents a hydrogen atom, alkyl of 1 to 4 carbon atoms or phenyl, $R_2$ represents hydrogen, and, except when $R^1$ is hydrogen, also represents alkyl of 1 to 4 carbon atoms, or $R^1$ and $R^2$ together represent tetramethylene, $R^3$ and $R^4$ are the same or different and each independently represents alkyl of 1 to 4 carbon atoms, cycloalkyl, substituted or unsubstituted phenyl or benzyl, or together they represent tetramethylene or pentamethylene, and M represents a divalent copper, zinc, cobalt or, in particular, nickel cation.

$R^2$ is preferably hydrogen and $R^3$ and $R^4$ are preferably the same.

Each of $R^1$ and $R^2$ is preferably a hydrogen atom, alkyl of 1 to 2 carbon atoms, phenyl, and together represent tetramethylene.

$R^3$ and $R^4$ can have the same meanings as previously given for $R^1$ and $R^2$ and, in addition, represent cycloalkyl containing preferably 5 or 6 ring members, a substituted or unsubstituted phenyl and benzyl group or represent the pentamethylene radical. Where the phenyl and benzyl groups are substituted, preferred substituents are alkyl radicals of 1 to 6 carbon atoms, for example methyl, ethyl, propyl, isopropyl, butyl, tert. butyl, hexyl.

Suitable values for $R^1$ and $R^2$ are, for example, hydrogen, methyl, ethyl, propyl, isopropyl, butyl, tert. butyl.

Suitable groups and radicals represented by $R^3$ and $R^4$ are in addition: phenyl, benzyl, methylphenyl, dimethylphenyl, butylphenyl, methylbutyl, propylphenyl, hexylphenyl, dodecyclphenyl, p-methylbenzyl, decylbenzyl, cyclopentyl, cyclohexyl, cycloheptyl, methylcyclohexyl.

If X is aminomethyl, $R^1$ and $R^2$ preferably represent a hydrogen atom and M represents in particular a nickel atom.

$R^1$ represents in particular hydrogen, methyl, ethyl, phenyl, or together with $R^2$ represents tetramethylene, and each of $R^3$ and $R^4$ represents methyl, ethyl, phenyl, or together they represent pentamethylene.

The compounds of the present invention can be illustrated by the following structural formula

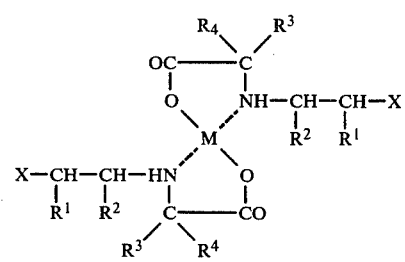

The compounds of the formula I are obtained by reacting aminocarboxylic acids of the formula II

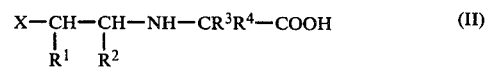  (II)

wherein X and $R^1$ to $R^4$ are as defined hereinbefore, with metal salts or metal complexes, in particular those of divalent nickel, zinc, copper or cobalt.

The aminocarboxylic acids of the formula II are to some extent known and to some extent new compounds. N-Hydroxyethyl-α-aminocyclohexanecarboxylic acid and 1-methyl-1-hydroxyethylaminopropionic acid are described, for example, in A. I. Kipriyanov, et al, Z. obsc. Chim. 2 (1932). page 585 ff.

A general, new process consists in decomposing aqueous solutions of aminoalkylated or hydroxyalkylated hydantoins of the formula III

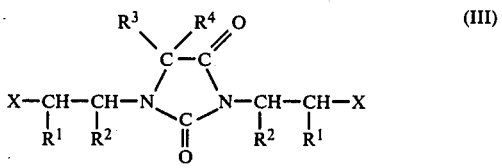

wherein $R^1$ to $R^4$ and X are as defined in formula I, in the presence of a metal hydroxide, and isolating the aminocarboxylic acid by known methods. The reaction is normally carried out with barium hydroxide at temperatures from 80° C. to below the decomposition point of the hydantoins of the formula III and under normal pressure or overpressure. The working up is advantageously effected by neutralising the reaction mixture with carbon dioxide, whereupon the excess barium hydroxide precipitates as carbonate and can be filtered off. Afterwards the desired aminocarboxylic acid can be isolated from the solution by precipitating it with acetone. However, it is also possible to evaporate the water and ethanolamine which has formed and to purify the residue by recrystallisation. Further details can be inferred from Examples 1 and 2.

Hydroxyalkylated and aminoalkylated hydantoins of the formula III, which are required for the process of this invention, are known compounds which are obtained by reacting epoxides with hydantoins. Examples are described in German Offenlegungsschriften Nos. 1,812,003, 1,912,026 and 1,966,743. The manufacture of N-bis-γ-aminopropylhydantoins by reacting acrylonitrile with corresponding hydantoins is known.

Suitable metal salts of nickel, zinc, copper and cobalt for obtaining the metal complexes of this invention are derived, for example, from the inorganic acids, such as carbonic acid, sulphuric acid, phosphoric acid, phosphorus acid, hydrochloride acid, hydrobromic acid, nitric acid, hydrogen sulphide, and from organic acids, such as monocarboxylic or dicarboxylic acids, for example formic acid, acetic acid, propionic acid, benzoic acid, or from sulphonic acids or phosphonic acids. It is also possible to use metal hydroxides instead of the salts. Among the suitable metal complexes paticular mention may be made of the acetylacetonates.

Preferred salts are the carbonates of nickel, zinc, copper and cobalt.

The process for the manufacture of the complexes of this invention is carried out as a rule in two advantageous embodiments, either in solution or in the melt. Suitable solvents are water or polar organic solvents, such as dimethyl formamide, dimethyl sulphoxide or hexamethylphosphoric triamide. The reaction is carried out normally at elevated temperatures of about 50°–250° C., depending on the nature of the solvent. If water is used as solvent, metal carbonates are preferably used as metal salts. Since the acid corresponding to the metal salt is liberated during the reaction in solution, it is advisable to add an acid acceptor, such as sodium bicarbonate, or to carry out the reaction in a buffered solution. The complexes are isolated as a rule by filtering off the crystalline products. The reaction in the melt is normally carried out when chelating metal complexes, such as acetylacetonates, with the aminocarboxylic acids of this invention. The temperature here can be up to more than 50° C. above the melting point of the metal complex.

The compounds of the invention are coloured and crystalline, and they are characterised by a surprisingly high stability, in particular an excellent resistance to heat under oxydative influences. They are also soluble in many starting components for the polymer manufacture, for example in glycols. They are therefore suitable for the manufacture of chelate polymers with high molecular weights by conventional processes.

Because of their stability, the compounds of the present invention, for example the nickel salts, can also be used as light stability agents in polyolefins, such as polyethylene, polypropylene, polybutylene, or copolymers. Further fields of use are as biocides, for example in antifouling paints, in which case, for example, the diols of the formula I can also be polymerised into the coating.

In addition to their stability, the compounds of the invention have surprisingly good solubility in monomers, for examples diols and diamines which are used for obtaining polymers derived from polyesters, polyamides, polyurethanes or polyureas. They are therefore eminently suitable as comonomers for manufacturing these polymers, which are obtained as polymers containing metal ions in the polymer chain.

The present invention therefore also provides copolymers which contain metal ions and belong to the group of the linear and crosslinked polyurethanes, the linear polyesters, polyamides, polyureas, polyester amides and polyurethane ureas, and which contain up to 15 molar percent, referred to the polymer, of divalent radicals of at least one metal complex of the formula I.

Preferably the copolymers of the present invention contain up to 10 molar percent, in particular 2.5 to 7.5 molar percent, of radicals of a metal complex of the formula I.

By polyester amides are meant copolymers of dicarboxylic acids, optionally hydroxycarboxylic acids or aminocarboxylic acids as co-component, diols and diamines. By polyurethane ureas are meant copolymers of at least difunctional isocyanates and amines and polyols.

The linear polyesters are based on aliphatic and aromatic dicarboxylic acids, diols, and, optionally, hydroxycarboxylic acids as comonomers. They can in this connection be monopolyesters or copolyesters. It is therefore possible for the polyesters to contain one or more dicarboxylic acids, one or more diols, and, in addition, one or more hydroxycarboxylic acids.

Suitable dicarboxylic acids are linear and branched, saturated and unsaturated aliphatic dicarboxylic acids, aromatic dicarboxylic acids, cycloaliphatic dicarboxylic acids and dicarboxylic acids and dicarboxylic acids which contain amido or imido groups or N-heterocyclic rings.

Examples of possible aliphatic dicarboxylic acids are: malonic acid, dimethyl malonic acid, succinic acid, octadecylsuccinic acid, pimelic acid, adipic acid, trimethyladipic acid, sebacic acid, azelaic acid, maleic acid, fumaric acid, methylmaleic acid, and dimeric acids (dimerisation products of unsaturated aliphatic carboxylic acids, such as oleic acid).

Examples of possible cycloaliphatic dicarboxylic acids are: 1,3-cyclobutanedicarboxylic acid, 1,3-cyclopentanedicarboxylic acid, 1,3- and 1,4-cyclohexanedicarboxylic acid, 1,3- and 1,4-dicarboxylmethylcyclohexane, 4,4'-dicyclohexyldicarboxylic acid.

Examples of suitable dicarboxylic acids are: terephthalic acid, isophthalic acid, o-phthalic acid, 1,3-, 1,4-, 2,6- or 2,7-naphthalenedicarboxylic acids, 4,4'-diphenyldicarboxylic acid, 4,4'-diphenylsulphonedicarboxylic acid, 1,1,3-trimethyl-5-carboxyl-3-(p-carboxylphenyl)-indane, 4,4'-diphenyl ether dicarboxylic acid, bis-p-(carboxylphenyl)-methane.

It is known that dicarboxylic acids which contain amido groups are obtained by reacting diamines or aminocarboxylic acids with dicarboxylic acids or derivatives thereof that form the carboxy amide group. These dicarboxylic acids are described, for example, in German Offenlegungsschrift Nos. 2,453,448, 2,150,808 and in U.S. Pat. No. 2,925,405.

Dicarboxylic acids which contain imido groups are also known and are described, for example, in German Offenlegungsschrift No. 2,453,448 and in U.S. Pat. No. 3,217,014. N-Carboxyl-methyltrimellitic imide may be cited as an example.

Possible hydroxycarboxylic acids are aliphatic, cycloaliphatic, cycloaliphatic-aliphatic, aromatic and aromatic-aliphatic acids. As examples there may be mentioned: glycollic acid, β-propionic acid, β- or γ-hydroxybutyric acid, p-hydroxy-cyclohexanecarboxylic acid, parahydroxymethyl-cyclohexanecarboxylic acid, m- or p-hydroxybenzoic acid, p-hydroxyphenylacetic acid.

Suitable diols are the aliphatic glycols, in particular those containing 2 to 10 carbon atoms in the molecule, cycloaliphatic and cycloaliphatic-aliphatic diols, such as 1,4-dihydroxycyclohexane, 1,4-dihydroxymethylcyclohexane, aromatic and aromatic-aliphatic diols, such as hydroquinone, p-xylylene glycol or 2,5-dichloro-p-xylylene glycol, polyoxyalkylene glycols, such as diethylene glycol, triethylene glycol, polyethylene glycol, bis(p-hydroxyphenyl)methylene, bis(p-hydroxyphenyl)ethylidene or bis(p-hydroxyphenyl)propylidene and bis-(p-hydroxyphenyl)sulphone or bis(p-hydroxyphenyl) ether.

Further suitable diols are those that contain N-heterocyclic rings. These are principally the β-hydroxyalkylated hydantoins, alkylene-bishydantoins and benzimidazolones, which can be partially or completely halogenated, in particular chlorinated and/or brominated, in the phenyl nucleus. These diols are described, for example, in German Offenlegungsschrift No. 2,453,448.

Preferably the polyesters contain at least 40 molar percent of terephthalic acid and at least 40 molar percent of aliphatic diols which contain 2 to 10, especially 2 to 4, carbon atoms, or 1,4-dihydroxymethylcyclohexanes, referred to the pure polyester. In particular, the polyesters contain only linear aliphatic diols containing 2 to 4 carbon atoms and one diol of the formula I.

The copolyesters of the present invention are obtained by known methods by polycondensing dicarboxylic acids, or the polyester-forming derivatives thereof, with diols and a metal complex of the formula I.

The known processes for obtaining the polyesters of this invention are, for example, solvent or azeotropic condensation, interface condensation, melt or solid phase condensation and also combinations of these methods, depending on which polyester-forming derivatives and reaction catalysts are used.

As polyester-forming derivatives of the dicarboxylic acids there are used principally the low molecular dialkyl esters containing 1 to 4 carbon atoms in the molecule, preferably dimethyl ester or diphenyl ester. The acid dihalides, in particular the acid dichlorides and anhydrides, are also suitable.

The polyesters of the present invention can be obtained by esterifying dicarboxylic acids, or transesterifying low molecular dialkyl esters thereof, at 50° to 250° C., with diols and a metal complex of the formula I, in an inert atmosphere, for example in an atmosphere of nitrogen, in the presence of catalysts and while simultaneously removing the water or alkanol that forms, and subsequently carrying out the polycondensation at temperatures below the decomposition temperature and under reduced pressure, in the presence of specific catalysts, until the polycondensation products have the desired viscosity.

As esterification catalysts it is possible to use, in known manner, amines, inorganic or organic acids, for example hydrochloric acid or p-toluenesulphonic acid, or also metals or metal compounds which are also suitable as transesterification catalysts.

Since some catalysts tend to promote the transesterification and others the polycondensation, it is advantageous to use a combination of several catalysts. Suitable transesterification catalysts are, for example, the oxides, salts or organic compounds of the metals calcium, magnesium, zinc, cadmium, manganese, titanium and cobalt. The metals themselves can also be used as catalysts. The polycondensation is catalysed, for example, by metals like lead, titanium, germanium, tin and, in particular, antimony or compounds thereof. These catalysts can be added to the reaction mixture together or separately.

These catalysts are used in amounts of approximately 0.001 to 1 percent by weight, referred to the acid component.

In the manufacture of the polyesters of this invention it is particularly advantageous to use those catalysts which promote both the transesterification and the polycondensation. Such catalysts are primarily mixtures of different metals or metal compounds as well as corresponding metal alloys.

The polycondensation is carried out until the polyesters have attained the desired viscosity. Depending on the nature of the catalyst used and on the size of the batch, the reaction times are from about 30 minutes to several hours. The resultant polyester melt, after it has been removed from the reaction vessel and cooled, is granulated or shredded in the usual way.

Another process for obtaining the polyesters of this invention consists in polycondensing dicarboxylic dihalides, preferably the dichlorides, with the diols in the presence of a basic catalyst in the temperature range from 0° to 100° C., with attendant dehydrohalogenation. Preferably amines or quaternary ammonium salts are used as basic catalysts. The amount of basic catalyst can be from 0.1 to 100 molar percent, referred to the acid halides. This process can be carried out in the presence of a further suitable solvent in which the metal complexes also dissolve.

The polycondensation can also be carried out in such a manner that the starting compounds are initially condensed in the melt to a certain viscosity. Then the precondensate obtained is granulated, for example using an underwater granulator, and the granulate is dried and then subjected to a solid phase condensation in vacuo and at a temperature below the melting point of the granulate. Higher viscosities can thereby be attained.

A particularly advantageous process for obtaining the polyesters of the present invention consists in starting from a polyester, in particular one based on polyalkylene terephthalate, which has a relative viscosity of 1.3 to 4, and fusing and reacting it together with the metal complex until the metal complex is incorporated into the polyester. The viscosity of the polyester falls in the process. However, it can be raised again by subsequently subjecting the resultant granules to an aftercondensation, for example a solid phase condensation.

It is also possible to add the metal complex of the formula I in solution to the polyester, preferably in a diol from which the polyester is synthesised, and afterwards to heat and react it.

The polyamides according to the invention are obtained in principle by the same or similar processes as the polyesters. To this end the same dicarboxylic acids or polyamide-forming derivatives thereof, such as diesters or dihalides, are polymerised with diamines and diamines of the formula I.

The polyamides are preferably synthesised from terephthalic acid, aliphatic dicarboxylic acids which preferably contain 6 to 12 carbon atoms, alkylenediamines of 2 to 12, in particular 6 to 12, carbon atoms, and cycloaliphatic diamines.

In addition to terephthalic acid, particularly preferred components are adipic acid, hexamethylenediamine, which can also be alkylated, and cyclohexane-bis-methylene as well as 1,12-dodecylenediamine. Polyamides which are based on polyamide 66 are especially preferred.

The diamines of the formula I can also be polymerised into the polyamide by the previously mentioned process by fusing them together with a polyamide.

The polyurethanes of the present invention are obtained by the polyaddition of polyols and diols of the formula I to polyfunctional isocyanates. As a rule, the procedure to be followed is that the reaction is initiated at low temperatures in the region of 50° C. and afterwards brought to completion at temperatures up to those below the decomposition temperature of the resultant polymer.

Both aliphatic and aromatic diisocyanates or triisocyanates are suitable, for example diphenylmethane-4,4'-diisocyanate, hexamethylene diisocyanate, isophoron diisocyanate, 1-methyl-cyclohexyl-2,6-diisocyanate, toluylene-2,4- or -2,6-diisocyanate, naphthalene-1,5-diisocyanate or triphenylmethane-4,4',4''-triisocyanate.

Preferably aliphatic diols are used besides the diisocyanates for obtaining the linear polyesters, for example alkylenediols of 2 to 12 carbon atoms, in particular butane-1,4-diol, polyethers of these diols, such as bis-ethylene glycol, triethylene glycol, polyethylene oxides, polypropylene oxides, polybutylene oxides, polytetrahydrofuran, polythioethers, for example of monothioethylene glycol, polyacetals which are derived from formaldehyde or other aldehydes, and linear polyesters which are obtained from dicarboxylic acids, in particular adipic acid and an excess of diols.

For obtaining branched polyurethanes there are used at least trifunctional polyols, such as glycerol, trimethylolpropane, pentaerythritol, and branched polyesters which are obtained by reacting dicarboxylic acids, for example adipic acid and phthalic acid, with an excess of diols or triols or tetrols. The molecular weight of the polymeric dihydroxy or polyhydroxy component is in general between about 800 and 3000.

The polyureas of the present invention are obtained by reacting diisocyanates with diamines and diamines of the formula I in a manner similar to that employed in the manufacture of the polyurethanes. Particularly suitable amines are aliphatic amines and cycloaliphatic amines of 2 to 12 carbon atoms and aromatic amines, for example phenylenediamine.

In the working up of the polyester melt, or before the polymerisation reaction or after the completion of the reaction in the melt phase, it is possible to add to the reaction mass inert additives of all kinds, for example reinforcing fillers, in particular 5 to 50 percent by weight of sized glass fibres, inorganic or organic pigments, fluorescent brighteners, matting agents, crystallisation promoters, mould release agents or flame-proofing agents.

If the polymerisation is carried out batchwise, the inert additives can be added during the final condensation steps, for example in the solid phase condensation or also at the conclusion of the melt condensation.

The polymers of the present invention of which the thermoplastic polyamides, polyurethanes, and, in particular, polyesters, are preferred, are partly crystalline to amorphous coloured polymers, depending on which starting components are used and in what ratios they are used. They are preeminently suitable for manufacturing moulded articles of all kinds by the customary moulding processes, such as casting, moulding, laminating, injection moulding, injection blow moulding and extruding. It is also possible to use them for surface coating by the customary methods, for example sintering, electrostatic coating or dipping processes.

The unsaturated polyesters can be further processed with conventional coreactants, such as polystyrene, and with conventional processing assistants to give moulded articles of crosslinked polyesters.

Examples of moulded articles are technical apparatus parts, such as casings or gear wheels, containers, sheets, boards, films, filaments and semi-finished products which can be machined.

The polymers of the present invention have a surprisingly high E-module and stiffness as well as good electrical surface properties.

The following Examples will serve to illustrate the invention. The polyesters are characterised more closely by means of the following characteristic data, which are measured by differential thermoanalysis from a sample which has been tempered for 3 minutes at 30° C. above the melting point or softening point and then rapidly chilled. The chilled sample is heated by means of a Perkin-Elmer "DSC-1B" differential scanning calorimeter with a heating speed of 16° C./min. The thermogram of the sample shows the glass transition temperature (T), the crystallisation temperature ($T_k$) and the melt temperature ($T_s$) and the softening temperature ($T_e$). The critical moment in the sudden increase of the specific heat in the thermogram indicates the glass transition temperature, the tip of the exothermic peak indicates the crystallisation temperature and the tip of the endothermic peak indicates the melt temperatures. The relative vicosity of the polycondensates is determined in solutions of 1 g of polyester in 100 ml of a mixture consisting of equal parts of phenol and tetrachloroethane at 30° C.

The molar percentages refer to the polymer.

(A) MANUFACTURE OF THE β-HYDROXYETHYL-α-AMINO ACIDS

(a) Manufacture of N-β-hydroxyethyl-α-amino-cyclohexanecarboxylic acid 24.3 g of 1,3-dihydroxyethyl-5,5-pentamethylene hydrantoin together with 185 g of $Ba(OH)_2 \times 8\ H_2O$ and 300 ml of water are kept for 3 hours at 160° C. in a shaking autoclave. Carbon dioxide is passed into the chilled reaction mixture until a pH of 7 is attained, then the precipitated $BaCO_3$ is filtered off with suction and washed repeatedly with water. The filtrate is concentrated to dryness and recrystallised from methanol/water (5:1).

Yield: 15.8 g=94% of theory (flakes).
Melting point: 282°–285° C. (sublimation).
Acid number: Calculated—299.5; Found—305.

The infrared and nuclear magnetic resonance spectra accord with the structure of the above product.

(b) Manufacture of N-β-hydroxyethyl-1-methyl-α-aminopropionic acid 78 g of 1,3-dihydroxyethyl-5,5-dimethyl hydantoin together with $Ba(OH)_2 \times 8\ H_2O$ and 300 ml of water are kept for 3 hours at 160° C. in a shaking autolave. Carbon dioxide is passed into the chilled reaction mixture until a pH of 7 is attained, then the precipitated $BaCO_3$ is filtered off with suction and repeatedly washed with water. The filtrate is concentrated to dryness and recrystallised from ethanol/water (8:1).

Yield: 80.7% of theory (needles).
Melting point: 285°–288° C. (sublimation).
Acid number: Calculated—380.9; Found—392.

The infrared and nuclear magnetic resonance spectra accord with the structure of the above product.

(B) MANUFACTURE OF THE METAL COMPLEXES

Example 1—Nickel-bis-(N-β-hydroxyethyl-α-aminocyclohexanecarboxylate)

16.71 g of N-hydroxyalkyl-α-amino-cyclohexanecarboxylic acid are dissolved in 200 ml of hot water and 5.89 g of nickel carbonate are added with stirring. Slight foaming occurs and a turquoise blue precipiate forms. Stirring is continued for 1 hour at 85° C. and the precipitate is collected by suction filtration. The substance is washed with cold water and acetone and dried overnight at 130° C.

Yield: 19.2 g=90.1% of theory.
Melting point: >300° C. (decomp.).
Ni.: Calculated—13.62%; Found—13.23%.

The heat resistance was measured by thermoanalysis (TA - 1, Mettler):

| | |
|---|---|
| start of the weight increase in air (definition: lowest decrease greater than 1°/₀₀/min) | 250° C. |
| temperature of the maximum change in weight in air | 285° C. |
| temperature of maximum change in weight in a nitrogen atmosphere | 300° C. |

Example 2—Nickel-bis-(N-β-hydroxyethyl-α-methyl-α-aminopropionate 18.8 g of N-hydroxyalkylamino-isobutyric acid are dissolved in water and 7.5 g of nickel carbonate are added. The mixture is heated, with stirring, to app. 85° C., when slight foaming occurs and the solution turns dark blue in colour. The solution is filtered hot and blue crystals fall out of the filtrate on cooling. These crystals are washed with a small amount of cold water and dried. The substance is dried overnight in vacuo at 130° C.

Yield: 16 g=71% of theory.
Melting point: >300° C. (with decomp.).
Ni: Calculated—16.74%; Found—16.5%.

Example 3—Copper-bis-(N-β-hydroxyethyl-α-aminocyclohexanecarboxylate)

5.6 g of N-hydroxyethylaminocyclohexanecarboxylic acid are dissolved in 200 ml of hot water and 1.85 g of copper carbonate are added with stirring. Slight foaming thereupon occurs and the solution turns dark blue in colour. The solution is filtered hot and, on cooling, blue crystals precipitate. These crystals are washed with a small amount of cold water and acetone. The substance is dried overnight at 130° C. in vacuo.

Yield: 5.4 g=82.7% of theory
Melting point: app. 190° C. (with decomp.)
Cu: Calculated—14.58%; Found—14.32%.

Example 4—Zinc-bis-(N-β-hydroxyethyl-α-methyl-α-aminopropionate)

A solution of 1.47 g of 1,3-dihydroxyethyl-5,5-dimethylamino acid and 1.6 g of zinc acetylacetonate in 100 ml of water is heated gradually to 50° C. with stirring. After a reaction time of 5 hours the batch is filtered and the filtrate is concentrated almost to dryness. The residue is washed repeatedly with acetone and filtered off with suction.

Yield: 1.6 g=89.6% of theory
Melting point: 223°–225° C.
Zn: Calculated—18.3%; Found—18.2%.

Example 5 (comparison example)

The heat resistance of the nickel compound of the invention and of nickel-bis-(N-β-hydroxyethyl-α-aminoacetic acid), identified as I in the Table, is determined in an atmosphere of nitrogen and in air by differential thermoanalysis (DTA) and differential thermogravimetry (DTG). It is evident from the Table that the heat resistance, and especially the resistance to the influence of heat and oxygen, of the compounds of the invention is improved.

| Determinants | I | Example 1 | Example 2 |
|---|---|---|---|
| Start of the decrease in weight in an $N_2$ atmosphere (6 1/h) - (1°/₀₀/min) (DTG) | 230 | 256 | 260 |
| Temperature of the maximum change in weight in an $N_2$ atmosphere (6 1/h) - DTG Exothermic procedure in dry air (6 1/h) | 282 | 300 | 290 |
| Start of the heat procedure under oxydative in- | 185 | 245 | 245 |

-continued

| Determinants fluences | I | Example 1 | Example 2 |
|---|---|---|---|

Example 6—Nickel-bis-(N-3-aminopropyl-α-aminocyclohexanecarboxylate 10 g (0.1 mole) of N-3-aminopropyl-α-aminocyclohexanecarboxylic acid are dissolved at 80° C. in 200 ml of water. On adding 5.9 g (0.05 mole) of nickel carbonate $CO_2$ evolves and a change in colour to blue occurs. Stirring is continued for half an hour at 80° C. and the solution is then concentrated to dryness. The residue is dissolved in 200 ml of absolute methanol and precipitated by adding acetone, to give a light blue compound which is dried in vacuo at 100° C.

Yield: 7.3 g = 32% of theory.
Melting point: from 265° C. with decomposition.
Nickel content (theory): 12.8%.
Nickel content (found): 12.4%.

Example 7—Polyester based on sebacic acid and ethylene glycol

Ethylene glycol (0.095 mole), sebacic dichloride (0.1 mole) and metalliferous nickel-bis-(N-β-hydroxyethyl-α-methyl-α-aminopropionate (compound 2) (0.005 mole) are put into a polycondensation apparatus equipped with gas inlet tube, stirrer and distillation head. The temperature is slowly increased with vigorous stirring and while introducing nitrogen. The exothermic condensation reaction starts at app. 30° C. and HCl gas evolves. A clear, green solution which slowly solidifies is obtained. While stirring and simultaneously introducing nitrogen the temperature is raised to 160° C., depending on the dicarboxylic chloride, and kept thereat for 2 hours. A vacuum is then slowly applied and after about half an hour nitrogen is blown into the apparatus. A light grey polyester with a relative viscosity of 1.08 is obtained.

Example 8—Polyester based on sebacic acid and ethylene glycol 20.225 g (0.1 mole) of sebacic acid, 0.0975 mole of ethylene glycol and 0.0025 mole of compound 2 are put into a polycondensation apparatus equipped with stirrer and distillation head. The bath temperature is increased to 180° C. while stirring and introducing nitrogen and a clear, green solution is obtained. After a reaction time of 2 hours, about 1.5 ml of water have distilled over. The bath temperature is then raised to 220° C. A vacuum is then slowly applied, in the process of which the batch becomes increasingly viscous. After a reaction time of 2 hours nitrogen is blown into the apparatus. A wax-like, light green polymer, which melts completely clear under the melting point microscope, is obtained with a melting point of 64°-69° C. The relative viscosity is 1.19.

A wax-like, green polyester with a relative viscosity of 1.43 is obtained by using 0.095 mole of ethylene glycol and 0.05 mole of compound 2 and otherwise carrying out the above procedure.

Example 9—Polyester based on polyethylene terephthalate

Dimethyl terephthalate (0.1 mole), ethylene glycol and the catalyst are put into a polycondensation apparatus equipped with stirrer and distillation head. The apparatus is strongly heated in an oil bath, with stirring, to 200° C., and the methanol which is liberated during the treansesterification is distilled off. After about 1 hour the methanol is completely distilled off—the amount of distillate is read off in a graduated receiving vessel. The mixture is then strongly heated to 240° C. and then compound 2 is added. The metal complex dissolves under these conditions within app. 1 hour. Subsequently a vacuum is applied which is gradually increased to $10^{-3}$ Torr. The polycondensation is complete after about 2 hours.

The amount of compound 2 added, the catalyst, and the properties of the polyesters obtained are indicated in Table 1.

Table 1

| Compound 2 (molar %) | Catalyst | relative viscosity | $T_G$ | appearance |
|---|---|---|---|---|
| 2.5 | MnOAc/$Sb_2O_3$ | 1.25 | 75 | green, crystalline |
| 2.5 | ZnOAc/$Sb_2O_3$ | 1.35 | 80 | green, crystalline |
| 2.5 | ZnOAc | 1.22 | 75 | green, crystalline |
| 2.5 | Ca-glycolate/$Sb_2O_3$ | 1.24 | 74 | green, crystalline |
| 2.5 | Ge(OR)$_4$ | 1.22 | 67 | green, crystalline |
| 2.5 | $Sb_2O_3$ | 1.43 | 70 | green, crystalline |
| 5 | Ca-glycolate/$Sb_2O_3$ | 1.20 | 70 | green, crystalline |

Example 10—Polyester based on polybutylene terephthalate 29.1 g (0.15 mole) of dimethyl terephthalate, 29.7 g (0.33 mole) of butanediol-1,4- and catalytic amounts of dibutyl tin oxide (DBTO) are put into a polycondensation vessel equipped with stirrer and distillation head. The bath temperature is increased to 200° C. while stirring and passing in nitrogen. The apparatus is kept at this temperature for 1 hour and app. 12 ml of methanol are distilled off. The bath temperature is then raised to 240° C. and compound 2 is added. The batch is kept for about 1 hour at 240° C. with stirring and then a vacuum is applied. The vacuum is increased to $10^{-3}$ Torr and after about 2 hours nitrogen is blown into the apparatus. The amount of compound 2 added, the catalyst, and the properties of the polyester obtained are indicated in Table 2.

Table 2

| Compound (molar %) | Catalyst | relative viscosity | $T_K$ °C. | $T_C$ °C. | appearance |
|---|---|---|---|---|---|
| 2.5 | ZnOAc/$Sb_2O_3$ | 1.44 | — | — | light grey, crystalline |
| 2.5 | Ca-glycolate/$Sb_2O_3$ | 1.69 | — | — | green, crystalline |
| 2.5 | Ge(OR)$_4$ | 1.34 | 31 | — | light green, crystalline |
| 2.5 | DBTO | 1.84 | 40 | 49 | light green, crystalline |
| 2.5 | DBTO | 1.99 | 35 | 45 | light green, crystalline |

Example 11—Polyester based on polyethylene terephthalate with compound 2 and a further component The procedure of Example 9 is carried out, but using the additional components listed in Table 3.

Table 3

| Co-component (molar %) | | Compound 2 (molar %) | Catalyst | relative viscosity | $T_G$ °C. | appearance |
|---|---|---|---|---|---|---|
| 10 | phenylindane-dicarboxylic acid | 2.5 | DBTO | 1.30 | 95 | olive crystalline |
| 12.5 | dimethyliso-phthalate | 2.5 | DBTO | 1.28 | 68 | crystalline green, amorphous |
| 12.5 | dimethyliso-phthalate | 2.5 | Ca-gly-colate $Sb_2O_3$ | 1.36 | 71 | green, amorphous |
| 12.5 | bisphenol-A-diglycol-ether | 2.5 | DBTO | 1.38 | 64 | olive amorphous |
| 7.5 | dimethyl sebacate | 2.5 | DBTO | 1.36 | 45 | olive green crystalline amorphous |

Example 12—Polyester based on polybutylene terephthalate 22 g of polybutylene terephthalate ($\mu$rel=2.20) and compound 2 are put into a polycondensation apparatus equipped with stirrer and distillation head. The apparatus is strongly heated to 250° C. and the reactants are fused while introducing nitrogen. A vacuum is then applied and after a reaction time of about half an hour a completely clear, green melt is obtained. After a further reaction time of 2 hours at 250° C. nitrogen is blown into the apparatus. Transparent, green polymers with a setting point of app. 223°–226° C. are obtained.

The amount of 2 added and the properties of the polyesters obtained are indicated in Table 4.

Table 4

| Compound 2 (% by weight) | Properties | | | |
|---|---|---|---|---|
| | relative viscosity | $T_K$ °C. | $T_G$ °C. | appearance |
| 4 | 1.82 | 39 | — | amorphous |
| 8 | 1.48 | 59 | 40 | amorphous |
| 16 | 1.42 | — | — | amorphous |
| 20 | 1.39 | — | 46 | amorphous |
| 24 | 1.24 | 91 | 50 | amorphous |

Example 13—Polyurethanes

A mixture of ethylene glycol and compound 2 is put into a reaction vessel equipped with stirrer, drip funnel and cooler. The mixture is heated to 55° C. with vigorous stirring. The diisocyanate (0.1 mole) is then slowly added dropwise in the course of about 1 hour and the temperature is raised to 200° C. during this time.

Composition and properties of the polyurethanes obtained are indicated in Table 5.

Table 5

| Compound 2 (molar %) | diisocyanate | $T_G$ °C. | relative viscosity | appearance |
|---|---|---|---|---|
| 2.5 | isophorondi-isocyanate | 109 | 1.22 | light green |
| 5 | isophorondi-isocyanate | 113 | 1.37 | light green |
| 2.5 | hexamethylene diisocyanate | — | — | green, inhomogeneous |

We claim:

1. A copolyester, having a relative viscosity of at least 1.08 as measured on a solution of 1 gram of polymer in 100 ml of a mixture consisting of equal parts of phenol and symmetrical tetrachloroethane at 30° C., which comprises the condensation product in about a 1:1 molar ratio of diacids (a) with diols (b) and (c) so that the composition of the copolyester comprises, with all mol % values based on the total polyester, in the diacid component of the polyester (a) 50 mol%, of radicals derived from one or more aliphatic, cycloaliphatic, aromatic or heterocyclic-aromatic dicarboxylic acid;

and in the diol component of the polyester (b) from 47.5 to 35 mol% of radicals derived from one or more aliphatic, cycloaliphatic, cycloaliphatic-aliphatic, aromatic, aromatic-aliphatic or heterocyclic-aliphatic diols; and (c) from 2.5 to 15 mol% of radicals derived from one or more metal complex, of an N-hydroxylalkylated, branched alpha-aminocarboxylic acid and a divalent metal cation, of the formula

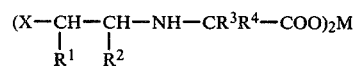

wherein

X represents hydroxyl, $R^1$ represents hydrogen, alkyl of 1 to 4 carbon atoms or phenyl, $R^2$ represents hydrogen, and with the proviso that when $R^1$ is alkyl of 1 to 4 carbon atoms or phenyl, $R^2$ also represents alkyl of 1 to 4 carbon atoms, or $R^1$ and $R^2$ together represent tetramethylene, $R^3$ and $R^4$ are the same or different and each independently represents alkyl of 1 to 4 carbon atoms, cycloalkyl of 5 or 6 carbon atoms, phenyl or benzyl, or said phenyl or said benzyl substituted by alkyl of 1 to 12 carbon atoms, or together with $R^3$ and $R^4$ represent tetramethylene or pentamethylene, and M represents a divalent copper, zinc, cobalt or nickel cation; or which comprises the condensation product in stoichiometric molar amounts of diacids (a), diols (c) and hydroxycarboxylic acids (d) so that the composition of the copolyester comprises, with all mol% values based on the total polyester, (a) from 2.5 to 15 mol% of radicals derived from one or more dicarboxylic acid (a) as defined above;

(c) from 2.5 to 15 mol% of radicals derived from one or more metal complex (c) as defined above; and (d) from 95 to 70 mol% of radicals derived from one or more aliphatic, cycloaliphatic, cycloaliphatic-aliphatic, aromatic or aromatic-aliphatic hydroxycarboxylic acid;

wherein the radicals (a), (b) and (c) or (a), (c) and (d) are attached through ester linkages in a random distribution.

2. A copolyester according to claim 1 wherein component (c) is present at from the 2.5 to 10 mol% level.

3. A copolyester according to claim 2 wherein component (c) is present at from the 2.5 to 7.5 mol% level.

4. A copolyester according to claim 1 wherein the polyesters are derived from components (a), (b) and (c).

5. A copolyester according to claim 4 wherein component (a) consists of 40 to 50 mol% of radicals derived from terephthalic acid.

6. A copolyester according to claim 4 wherein component (b) consists of radicals derived from an alkylene diol of 2 to 10 carbon atoms.

7. A copolyester according to claim 6 wherein the alkylene diol is of 2 to 4 carbon atoms.

8. A copolyester according to claim 1 where in the metal complex (c) $R^3$ and $R^4$ are alkyl of 1 to 2 carbon atoms, cycloalkyl of 5 to 6 carbon atoms, phenyl or benzyl; or said phenyl or said benzyl substituted by alkyl of 1 to 6 carbon atoms.

9. A copolyester according to claim 1 where in the metal complex (c) $R^2$ is hydrogen.

10. A copolyester according to claim 1 where in the metal complex (c) $R^3$ and $R^4$ are the same.

11. A copolyester according to claim 1 where in the metal complex (c) $R^1$ represents hydrogen, methyl, ethyl or phenyl, or together with $R^2$ represents tetramethylene.

12. A copolyester according to claim 1 where in the metal complex (c) each of $R^3$ and $R^4$ independently represents methyl, ethyl or phenyl, or together represent pentamethylene.

13. A copolyester according to claim 1 where in the metal complex (c) M is a nickel cation.

14. A copolyester according to claim 1 wherein the metal complex diol (c) is nickel-bis-(N-beta-hydroxyethyl-alpha-methyl-alpha-aminopropionate).

* * * * *